(12) United States Patent
Yetzbacher et al.

(10) Patent No.: US 9,915,563 B2
(45) Date of Patent: Mar. 13, 2018

(54) METHOD AND APPARATUS FOR MULTIPLEXED FABRY-PEROT SPECTROSCOPY

(71) Applicant: The United States of America, as represented by the Secretary of the Navy, Washington, DC (US)

(72) Inventors: Michael K. Yetzbacher, Burke, VA (US); Christopher W. Miller, Darnestown, MD (US); Michael J. Deprenger, Chantilly, VA (US); Andrew J. Boudreau, Washington, DC (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 76 days.

(21) Appl. No.: 15/046,835

(22) Filed: Feb. 18, 2016

(65) Prior Publication Data
US 2016/0161336 A1 Jun. 9, 2016

Related U.S. Application Data

(63) Continuation of application No. 14/282,067, filed on May 20, 2014, now Pat. No. 9,304,040.

(51) Int. Cl.
*G01J 3/26* (2006.01)
*G01N 21/45* (2006.01)
(Continued)

(52) U.S. Cl.
CPC .............. *G01J 3/26* (2013.01); *G01J 3/021* (2013.01); *G01J 3/45* (2013.01); *G01N 21/41* (2013.01); *G01N 21/45* (2013.01)

(58) Field of Classification Search
CPC .................................. G01J 3/26; G01N 21/45
See application file for complete search history.

(56) References Cited

U.S. PATENT DOCUMENTS

| 2007/0148760 A1* | 6/2007 | Klesel | G01J 1/42 |
| | | | 435/287.2 |
| 2011/0032531 A1* | 2/2011 | Simeoni | G01J 3/45 |
| | | | 356/455 |

(Continued)

OTHER PUBLICATIONS

Unser, "Sampling—50 Years After Shannon", Proceedings of the IEEE, vol. 88, No. 4, Apr. 2000 569.*

(Continued)

*Primary Examiner* — Dominic J Bologna
(74) *Attorney, Agent, or Firm* — US Naval Research Laboratory; Suresh Koshy

(57) ABSTRACT

A method of optical spectroscopy and a device for use in optical spectroscopy. The device includes a substrate, and a plurality of etalon cavities affixed to or coupled to the substrate. A signal is received from a Fabry-Perot interferometer. The signal is sampled using the device according to a generalized Nyquist-Shannon sampling criterion. The signal is sampled using the device according to a phase differential criterion for wave number resolution. An input spectrum for the signal is reconstructed based on the signal sampled according to the generalized Nyquist-Shannon sampling criterion and the signal sampled according to the phase differential criterion for wave number resolution.

4 Claims, 5 Drawing Sheets

(51) Int. Cl.
*G01N 21/41* (2006.01)
*G01J 3/02* (2006.01)
*G01J 3/45* (2006.01)

(56) References Cited

U.S. PATENT DOCUMENTS

| | | | | |
|---|---|---|---|---|
| 2011/0043823 A1* | 2/2011 | Hillmer | ............... | B82Y 10/00 356/519 |
| 2012/0327248 A1* | 12/2012 | Tack | ............... | G01J 3/26 348/164 |
| 2013/0120757 A1* | 5/2013 | Yu | ............... | A61B 3/102 356/479 |

OTHER PUBLICATIONS

Wyant, "Multiple Beam Interference" https://web.archive.org/web/20100708223128/http://wyant.optics.arizona.edu/MultipleBeamInterference/MultipleBeamInterferenceNotes.html, Jul. 8, 2010.*

* cited by examiner

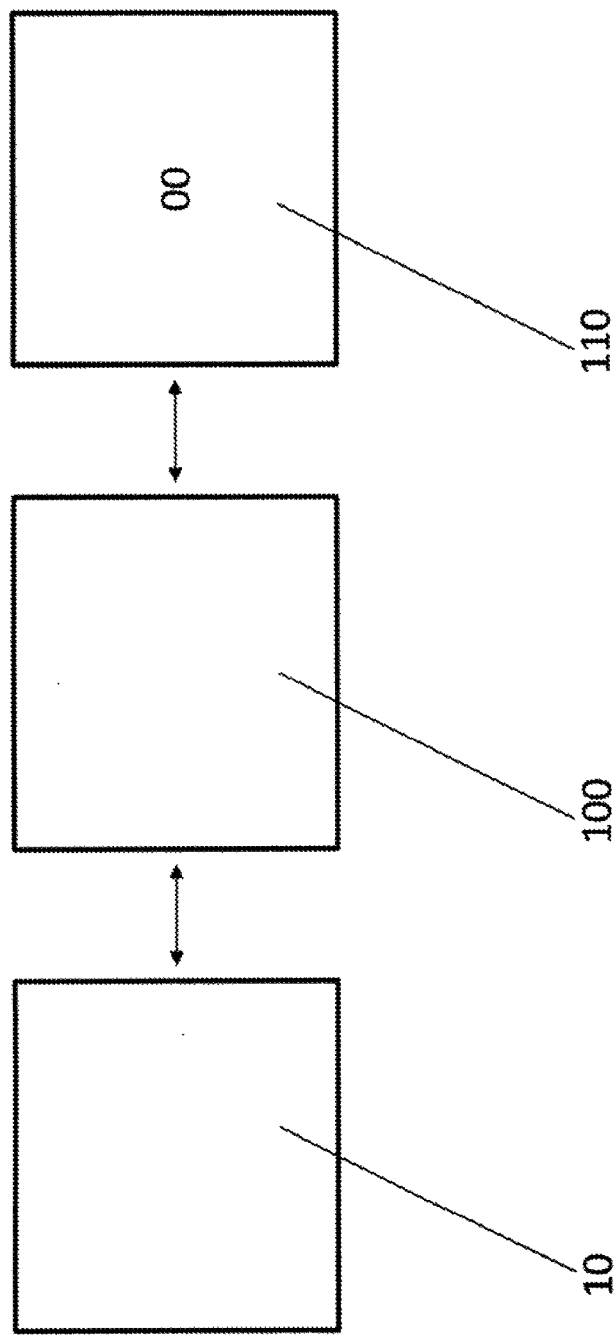

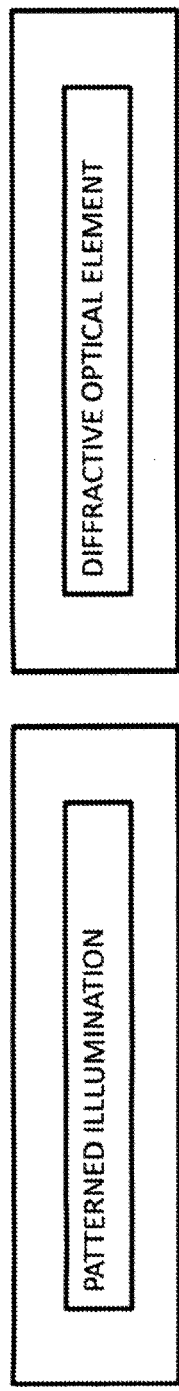
FIG. 4A
FIG. 4B
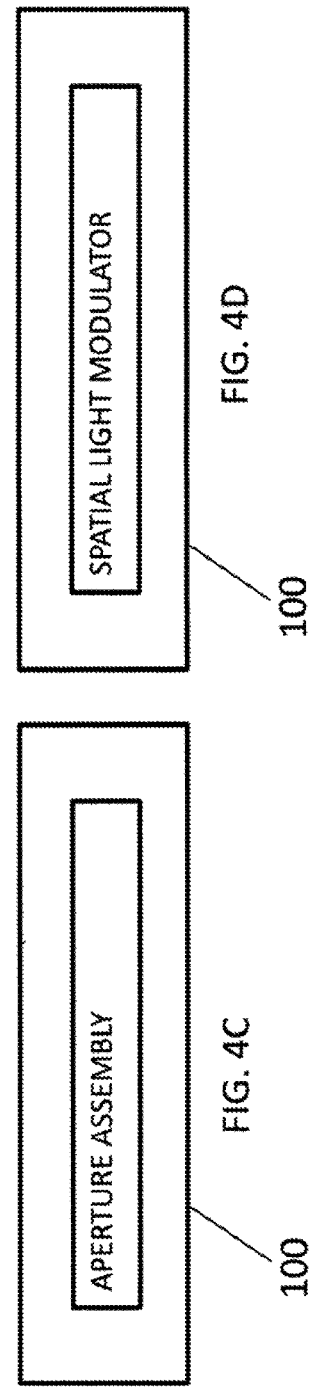
FIG. 4C
FIG. 4D

METHOD AND APPARATUS FOR MULTIPLEXED FABRY-PEROT SPECTROSCOPY

CROSS-REFERENCE TO RELATED APPLICATIONS

This application claims priority to U.S. Provisional Patent Application Ser. No. 61/825,577, entitled "ALGORITHM AND APPARATUS AND DEVICE PARAMETERS FOR MULTIPLEXED FABRY-PEROT SPECTROSCOPY," to Yetzbacher et al., which was filed on 21 May 2013 and is incorporated herein by reference. This application is a continuation application of U.S. patent application Ser. No. 14/282,067, entitled "METHOD AND APPARATUS FOR MULTIPLEXED FABRY-PEROT SPECTROSCOPY" and claims priority to this parent application.

BACKGROUND OF THE INVENTION

Field of the Invention

This invention relates general to method of optical spectroscopy and a device for use in optical spectroscopy, and in particular to method of optical spectroscopy capable of robustly recovering an optical spectrum or spectra associated with a scene using Fabry-Perot transmission data and a device for use in such optical spectroscopy.

Description of the Related Art

Several standard methods to measure spectra exist, using dispersive elements, interferometers, optical filters, and/or micro-optical components and associated transforms. All of these spectral measurement methods have been applied to imaging systems, but none has achieved a compact device with acceptable broadband performance.

Drawbacks of using dispersive elements and Michelson interferometers are the space required to spread the spectrum across several elements of a detector and the size and weight of dispersive elements, beamsplitters and their mechanical mounts.

The primary disadvantage of using macroscopic size optical filters is related to size and weight. Mosaic array filters have been used to reduce the size and weight of optical filter instruments. These have been used in imaging devices, but with limited spatial and spectral resolution. There is an unfavorable tradeoff space for using mosaic array filters for imaging spectroscopy. The efficiency/resolution tradeoff available with optical filters also offers design challenges. Similarly, lens-mounted optical filter arrays lead to the same disadvantageous tradeoff between spatial and spectral resolution.

Micro-optical components have been successfully used to eliminate the size and weight disadvantages of other techniques and have achieved high spectral resolution. Two examples of the micro-optical devices are described as follows and have been used in line-scanning mode for imaging spectroscopy, requiring the image to be translated across one dimension of the micro-optic. These devices have achieved spectral measurement by exploiting the interference between reflections from surfaces of the micro-optic.

First, in the case where the reflectance of each surface of the micro-optic has been low, Fourier Transform algorithms have been used. Such a micro-optical device uses a wedged micro-optic to create an interference pattern on a focal plane. The low reflectivity of the micro-optic creates a sinusoidal modulation of the light falling on the detector surface. Low reflectance leads to low fringe contrast in the measured interference pattern, leading to poor signal-to-noise ratio performance under typical field conditions. An additional limitation of this device is that the Fourier Transform processing has a defined resolution that is tied directly to the maximum thickness of the wedged micro-optic. Therefore, for any device thickness, the number of resolved spectral elements within the bandwidth of the detector is fixed and cannot be adjusted. Since the Fourier Transform calculates all frequencies between the Nyquist frequency and zero, the usable number of resolved spectral elements may be significantly smaller than the number of distinct measurements on the detector.

Second, in the case where the micro-optic device used high reflectance, good results have been obtained only over a limited bandwidth. Multiplexing of the spectrum is not taken into account. The spectral range of these devices is therefore limited to a single free-spectral range ("FSR") of the etalons. The spectral resolution of these devices is limited by the etalon finesse and the manufacturing tolerances for etalon arrays. The length difference between optical cavities in this device was on the order of a few nanometers. This type of device is difficult to manufacture, as step height must be accurately controlled, as each step is meant to provide unique information that is not duplicated by any other step. Further, the allowed usable step heights are limited to a few hundred nanometers, as in order to only be resonant with one optical frequency within the allowed bandwidth, the devices must have a FSR greater than the allowed bandwidth.

Another class of related devices the scanning Fabry-Perot interferometer. Scanning Fabry-Perot interferometers require optical inputs with bandwidth less than one FSR of the device. This is due to the ambiguity between signals arising from colors separated by one FSR for any Fabry-Perot interferometer. Fabry-Perot theory is only valid within one FSR, and is not capable of demultiplexing mixed signals.

BRIEF SUMMARY OF THE INVENTION

An embodiment of the invention includes a device. The device includes a substrate and a plurality of etalon cavities affixed to or coupled to the substrate. The plurality of etalon cavities include a plurality of cavity thicknesses. Each etalon cavity of said plurality of etalon cavities comprises a respective height value, said each etalon cavity of the plurality of etalon cavities has an associated next highest height value etalon cavity of the plurality of etalon cavities. The associated next highest height value etalon cavity of the plurality of etalon cavities comprising a next highest height value. The each etalon cavity of the plurality of etalon cavities having an associated next lowest height value etalon cavity of the plurality of etalon cavities. The associated next lowest height value etalon cavity of the plurality of etalon cavities comprising a next lowest height value. A difference between the next highest height value and the respective height value satisfies a generalized Nyquist-Shannon sampling criterion. A difference between the respective height value and the next lowest height value satisfies the generalized Nyquist-Shannon sampling criterion. The plurality of cavity thicknesses includes a maximum height value and a minimum height value. A difference between the maximum height value and minimum height value is at least a overall height range. The overall height range satisfies a phase differential criterion for wavenumber resolution.

Optionally, the substrate comprises a detector, and the generalized Nyquist-Shannon sampling criterion is represented as $$\delta \leq \frac{1}{4Fn\sigma_{max}},$$

where δ is a step size, F is a cavity finesse, n is a cavity refractive index, and $\sigma_{max}$ a maximum vacuum wavenumber to which the detector is sensitive.

Optionally, the phase differential criterion for wavenumber resolution is represented as $$d_r \leq \frac{1}{2Fn\Delta\sigma},$$

where $d_r$ is the said overall height range, F is a cavity finesse, n is a refractive index of a cavity, and Δσ is a vacuum wavenumber resolution of the device.

Optionally, the plurality of etalon cavities includes an evenly spaced plurality of etalon cavities or an unevenly spaced plurality of etalon cavities.

Optionally, the substrate includes an array detector or an image sensor. Optionally, the image sensor includes a two-dimensional focal plane array.

Optionally, the each etalon cavity of said plurality of etalon cavities includes two mirrors sandwiching a dielectric material. Optionally, each mirror of the two mirrors includes a flat, reflective surface and a reflective coating. Optionally, the reflective coating includes, for example, a metal coating or a dielectric layered coating. Optionally, each mirror of said two mirrors comprises a material boundary wherein a reflection is due to differences in refractive index. Optionally, the plurality of etalon cavities comprises a plurality of Fabry-Perot cavities.

Optionally, the plurality of etalon cavities includes a staircase cross-sectional profile.

Optionally, the device further includes imaging optics, a detector, and a scanner. Optionally, the imaging optics include patterned illumination, at least one diffractive optical element, at least one aperture assembly, at least one spatial light modulator, at least one micro-mirror array, at least one lens, or at least one mirror. Optionally, the scanner includes a fast scanning mirror scanner, a platform-motion scanner, a moveable diffractive optical element, a moveable refractive optical element, at least one translation stage providing motion for the imaging sensor, at least one rotation stage providing motion for the imaging sensor, or a gimbalized scanner. Optionally, the detector includes a point detector, a linear array detector, or a two-dimensional array detector.

Another embodiment of invention includes a method. A signal is received from a Fabry-Perot interferometer. The signal is sampled according to a generalized Nyquist-Shannon sampling criterion. The signal is sampled according to a phase differential criterion for wave number resolution. An input spectrum for the signal is reconstructed based on the signal sampled according to the generalized Nyquist-Shannon sampling criterion and the signal sampled according to the phase differential criterion for wave number resolution.

Optionally, a detector is provided. Also, the generalized Nyquist-Shannon sampling criterion comprises:

$$\delta \leq \frac{1}{4Fn\sigma_{max}},$$

where δ is a step size, F is a cavity finesse, n is a cavity refractive index, and $\sigma_{max}$ is a maximum vacuum wavenumber to which the detector coupled to the Fabry-Perot interferometer is sensitive.

Optionally, the phase differential criterion for wavenumber resolution comprises:

$$d_r \leq \frac{1}{2Fn\Delta\sigma},$$

where $d_r$ is said overall height range, F is a cavity finesse, n is a refractive index of a cavity, and Δσ is a vacuum wavenumber resolution.

Another embodiment of the invention includes a new method of optical spectroscopy capable of robustly recovering an optical spectrum or spectra associated with a scene using Fabry-Perot transmission data and a low-computational burden transform. This embodiment applies to signals derived from Fabry-Perot interferometers and arrays of Fabry-Perot etalons whether used in integrating or imaging configurations. It applies to continuous spectra or discrete spectral components calculated using multiplexed Fabry-Perot signals. An advantage of this embodiment is the disambiguation of spectra from etalon signals where the signal is derived from optical components having a spectral separation greater than the free-spectral range of the maximum cavity length. This advantage is achieved by measurement of a sufficient range and resolution of cavity lengths.

An embodiment of the invention is particularly suited for the recovery of moderate resolution (e.g., 5-500 $cm^{-1}$) optical spectra using compact staircase spectrometers. An embodiment of the invention is also useful for the recovery of any electromagnetic wave that can be made resonant with a cavity through reflections. That is, this embodiment of the invention is equally applicable to X-ray, Ultraviolet, infrared, microwave, and radio-wave spectroscopy.

An embodiment of the invention includes a compact, broadband, imaging spectrometer, and a new method appropriate for multiplexed Fabry-Perot spectroscopy. This embodiment allows for spectral measurement over the entire bandwidth of the detector while minimizing the effects of noise. The number of resolved spectral elements within the bandwidth of the detector is adjusted by adjusting the number of measurement points unlike in traditional Fourier Transform methods. The spectral resolution of this embodiment is not directly dependent on the step heights, therefore, the spectral fidelity of a device according to the instant invention is more decoupled from the precision of the manufacture than in prior art devices. A method according to the instant invention allows for an improvement in spectral resolution relative to Fourier Transform processing techniques. The spectral resolution gain over a Fourier Transform measurement of the same overall scan length is equal to the cavity finesse.

An embodiment of the instant invention method has one or more of six key advantages. First, this embodiment allows for an improvement in spectral resolution relative to Fourier Transform processing techniques. The spectral resolution gain over a Fourier Transform measurement of the same overall scan length is equal to the cavity finesse. Second, this embodiment allows for an increase in fringe contrast (and therefore signal-to-noise ratio) relative to micro-optic devices with effective two-beam interference. Third, this embodiment allows for disambiguation of Fabry-Perot transmission signals that have components separated by more than one free-spectral range of the maximum cavity retardation. This can be used to increase the usable bandwidth of Fabry-Perot instruments. Fourth, this embodiment allows for measurement of optical signals over the entire bandwidth of the detector. Fifth, this embodiment allows for instrument resolving power that does not depend on the physically resolvable step size; rather, it depends on the number of steps in the instrument. Sixth, this embodiment allows for tuning or designing the cavity finesse to optimize the recovered spectral resolution and maximum frequency for a particular signal-to-noise condition.

BRIEF DESCRIPTION OF THE DRAWINGS

FIG. 3 is a conceptual block diagram of a system including an embodiment of the instant invention.

FIGS. 4A-4G show by way of block diagram illustrative imaging optics according to embodiments of the instant invention, including patterned illumination, a diffractive optical element, an aperture assembly, a spatial light modulator, a micro-mirror array, a lens, and a mirror, respectively.

DETAILED DESCRIPTION OF THE INVENTION

Figure 1:
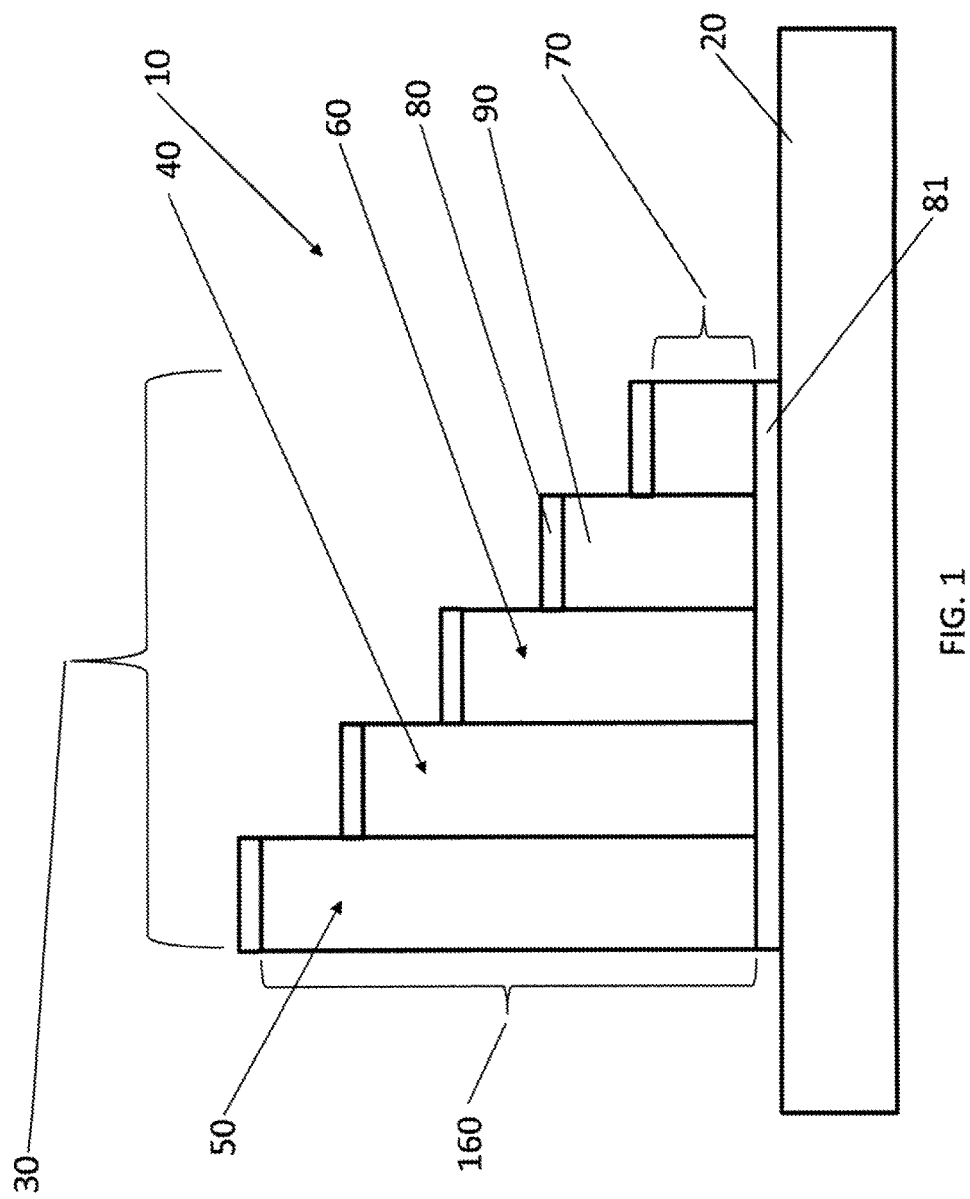
FIG. 1 is a conceptual, cross-sectional view of an instrumental embodiment of the instant invention, showing an ordered, evenly spaced array of Fabry-Perot etalons.
Figure 2:
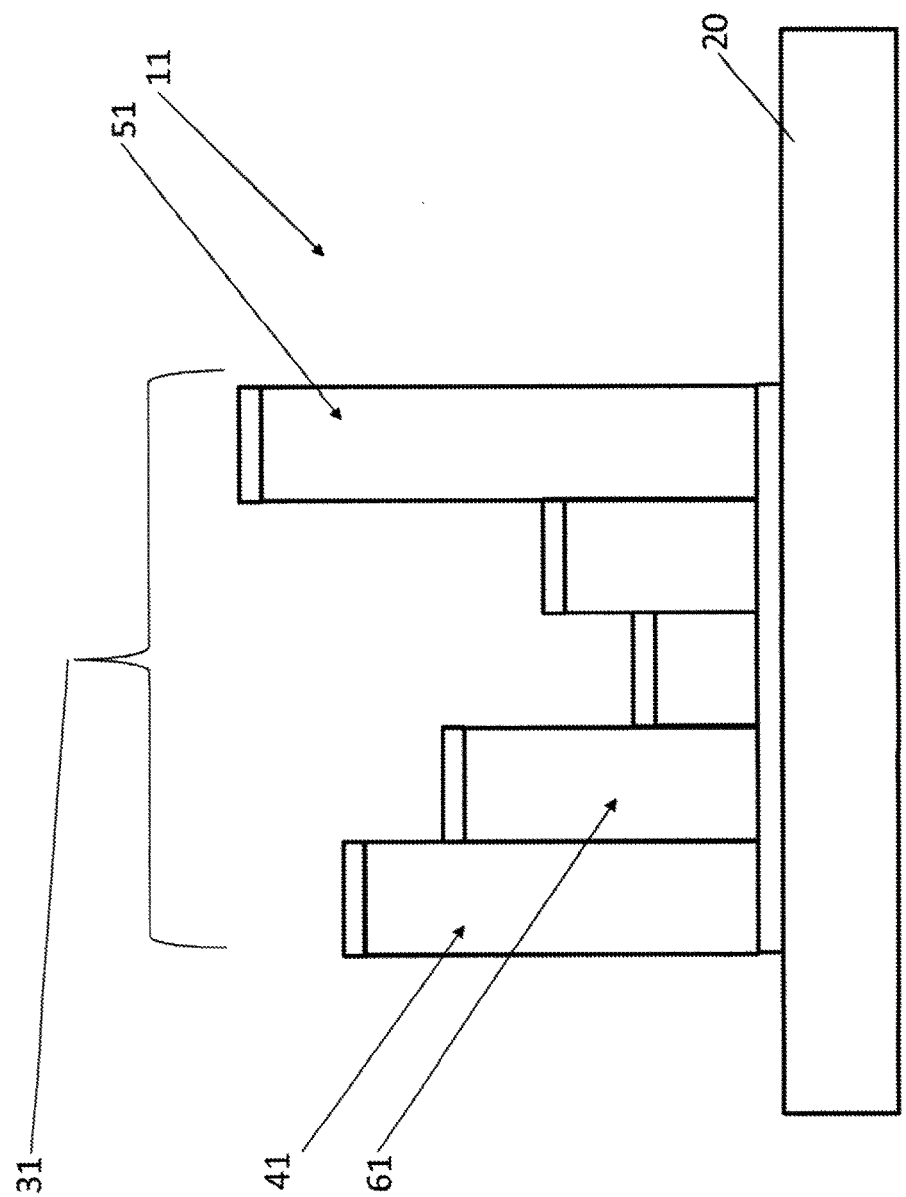
FIG. 2 is a conceptual, cross-sectional view of an unevenly spaced array of Fabry-Perot etalons.
Figure 4E:
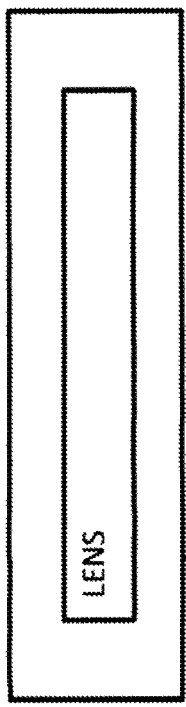
Figure 4F:
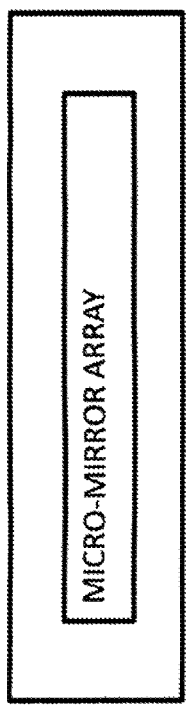
Figure 4G:
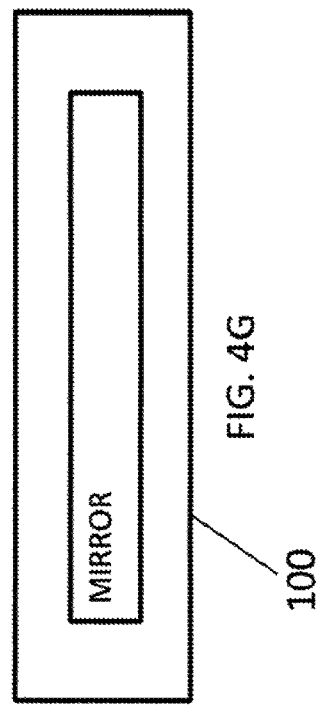

An embodiment of the invention includes a device 10, 11, and is described as follows by way of illustrative reference to FIGS. 1 and 2. The device 10, 11 includes a standard substrate 20 and a plurality of etalon cavities 30, 31 affixed to or coupled to the substrate. Although FIGS. 1 and 2 show the plurality of etalon cavities connected to the substrate, one of ordinary skill in the art will readily appreciate that an alternative embodiment includes the plurality of etalon cavities being operably coupled to the substrate, though not physically connected thereto. The plurality of etalon cavities 30, 31 include a plurality of cavity thicknesses. Each etalon cavity 40, 41 of said plurality of etalon cavities comprises a respective height value, said each etalon cavity of the plurality of etalon cavities has an associated next highest height value etalon cavity 50, 51 of the plurality of etalon cavities. The associated next highest height value etalon cavity of the plurality of etalon cavities comprising a next highest height value. The each etalon cavity of the plurality of etalon cavities having an associated next lowest height value etalon cavity 60, 61 of the plurality of etalon cavities. The associated next lowest height value etalon cavity of the plurality of etalon cavities comprising a next lowest height value. A difference between the next highest height value and the respective height value satisfies a generalized Nyquist-Shannon sampling criterion. A difference between the respective height value and the next lowest height value satisfies the generalized Nyquist-Shannon sampling criterion. The plurality of cavity thicknesses includes a maximum height value 160 and a minimum height value 70. A difference between the maximum height value and minimum height value is an overall height range. The overall height range satisfies a phase differential criterion for wavenumber resolution.

Optionally, the substrate comprises a standard detector, and the generalized Nyquist-Shannon sampling criterion is represented as $$\delta \leq \frac{1}{4Fn\sigma_{max}},$$

where $\delta$ is a step size, F is a cavity finesse, n is a cavity refractive index, and $\sigma_{max}$ is a maximum vacuum wavenumber to which the detector is sensitive.

Optionally, the phase differential criterion for wavenumber resolution is represented as $$d_r \leq \frac{1}{2Fn\Delta\sigma},$$

where $d_r$ is the said overall height range, F is a cavity finesse, n is a refractive index of a cavity, and $\Delta\sigma$ is a vacuum wavenumber resolution of the device.

Optionally, the plurality of etalon cavities includes an evenly spaced plurality of etalon cavities, such as shown by way of illustration in FIG. 1, or an unevenly spaced plurality of etalon cavities, such as shown by way of illustration in FIG. 2.

Optionally, the substrate 20 includes a standard array detector or a standard image sensor. Optionally, the image sensor includes a standard two-dimensional focal plane array.

Optionally, the each etalon cavity of said plurality of etalon cavities includes two standard mirrors 80, 81 sandwiching a standard dielectric material 90. Optionally, each mirror of the two mirrors includes a standard, flat, reflective surface and a standard reflective coating. Optionally, the reflective coating includes, for example, a standard metal coating or a standard dielectric layered coating. Optionally, each mirror of said two mirrors comprises a standard material boundary wherein a reflection is due to differences in refractive index. Optionally, the plurality of etalon cavities comprises a plurality of Fabry-Perot cavities.

Optionally, the plurality of etalon cavities includes a staircase cross-sectional profile, such as shown by way of illustration in FIG. 1.

Optionally, the device 10 includes standard imaging optics 100 and a standard scanner 110, wherein the substrate 20 includes a standard detector, such as shown by way of illustration in FIG. 3. Optionally, the imaging optics include standard patterned illumination, at least one standard diffractive optical element, at least one standard aperture assembly, at least one standard spatial light modulator, at least one standard micro-mirror array, at least one standard lens, or at least one standard mirror. Optionally, the scanner includes a standard fast scanning mirror scanner, a standard platform-motion scanner, a standard moveable diffractive optical element, a standard moveable refractive optical element, at least one standard translation stage providing motion for the imaging sensor, at least one standard rotation stage providing motion for the imaging sensor, or a standard gimbalized scanner. Optionally, the detector includes a standard point detector, a standard linear array detector, or a standard two-dimensional array detector.

Another embodiment of invention includes a method. A signal is received from a Fabry-Perot interferometer. The signal is sampled according to a generalized Nyquist-Shannon sampling criterion. The signal is sampled according to a phase differential criterion for wave number resolution. An input spectrum for the signal is reconstructed based on the signal sampled according to the generalized Nyquist-Shannon sampling criterion and the signal sampled according to the phase differential criterion for wave number resolution.

Optionally, a detector is provided. Also, the generalized Nyquist-Shannon sampling criterion comprises:

$$\delta \le \frac{1}{4Fn\sigma_{max}},$$

where $\delta$ is a step size, F is a cavity finesse, n is a cavity refractive index, and $\sigma_{max}$ is a maximum vacuum wavenumber to which the detector coupled to the Fabry-Perot interferometer is sensitive.

Optionally, the phase differential criterion for wavenumber resolution comprises:

$$d_r \le \frac{1}{2Fn\Delta\sigma},$$

where $d_r$ is said overall height range. F is a cavity finesse, n is a refractive index of a cavity, and $\Delta\sigma$ is a vacuum wavenumber resolution.

An embodiment of the instant invention is an ordered and evenly spaced array of Fabry-Perot etalons, such as shown in FIG. 1. This device uses an evenly spaced, ordered array of etalons and can be used to measure the signal of multiple order etalons. This device optionally has multiple optical frequencies resonant with any number of etalon cavities. This embodiment also has the etalons in close contact with a two-dimensional image sensor. In this configuration, the device can be used as a line scanning, imaging spectrometer when coupled to imaging optics, or a standalone spectrometer. When used as an imaging spectrometer, a component of a scene can be scanned across each etalon. Alternatively, lines of an image can be scanned across the etalon staircase The signal from incident light with a spectrum, $f(\sigma)$, transmitted through a Fabry-Perot cavity of length, l, is given by $$(Tf)(l) = \int_{\sigma_{min}}^{\sigma_{max}} dl K(l, \sigma) f(\sigma), \quad (1)$$

where $\sigma$ is the vacuum wavenumber (inverse of the vacuum wavelength), and $\sigma_{min}$ and $\sigma_{max}$ are the minimum and maximum vacuum wavenumbers to which the signal is sensitive. The kernel of equation (1), $K(l,\lambda)$, is given by the Airy function, $$K(l, \sigma) = \frac{1}{1 + F\sin^2(4\pi n\sigma l)} \quad (2)$$

where the Fabry-Perot cavity has an optical refractive index, n, and coefficient of finesse, F. For an ideal Fabry-Perot cavity, the coefficient of finesse is given by, $$F = \frac{4R}{(1-R)^2} \quad (3)$$

where R is the reflectance of the mirrors of the cavity.

Methodology

An embodiment of the invention includes an inventive methodology, wherein matrix multiplication of the measured etalon signal of an object, $(Tf)(l)$ is used to recover the spectrum, $f(\sigma)$. The derivation of the matrix is achieved by a solution of Equation (1). Equation (1) is a Freedholm integral equation of the first type. The existence of a solution is guaranteed, but the numerical stability of a solution requires that certain conditions be met. These conditions will be discussed in the next section.

The specific solution of equation (1) is an important part of any implementation of an embodiment of the invention. Solutions to equation (1) can take a variety of forms. A simple solution is to calculate the discretely sampled matrix $K(l,\sigma)$, and numerically invert it. This can be stably performed by using a singular value decomposition, and the accuracy of inverse transform obtained by this method is often satisfactory. Another approach is to calculate the singular value expansion of a continuously sampled $K(l,\sigma)$, e.g., with the method of moments. Once obtained, the continuous functions in l and $\sigma$ can be subsampled to recover signals on the appropriate axis. While the solution to equation (1) may be done by a computationally intensive method, the application of that solution to measured signals is a relatively quick matrix multiplication of the measured signal vector. Any method of solution for equation (1) that creates a matrix that can be applied to signals or a transform that yields coefficients for a set of continuous functions in $\sigma$ according to the conditions described below is a valid application of an embodiment of the invention.

Although a simple inversion of the sampling matrix is described above to calculate the inverse transform, one of ordinary skill in the art will readily appreciate alternative standard methods of calculating the inverse transform are possible, e.g. Singular Value Expansion of the Airy function, analytic solutions, etc.

Device Parameters for Stability of the Matrix Multiplication:

As the physical parameters of a Fabry-Perot device alter the kernel of equation (1), the physics of any Fabry-Perot device must be taken into account for a solution of equation (1). While a solution to equation (1) can always be calculated, there are some solutions that are more stable than others. Conditions necessary for accuracy and resistance to noise for the transform matrix are discussed as follows.

In general, the refractive index and cavity reflectivity will be functions of the optical frequency. Even in the case where the refractive index and cavity reflectivity are constant across the bandwidth of interest, the conditions for stable solutions to equation (1) depend on the physics of the measurement and are summarized as follows.

1. Sampling density and maximum wavenumber: The sampling density in l is required to satisfy the Nyquist-Shannon sampling limit for all frequencies present. The form of equation (2) obscures the frequency components present. For an ideal Fabry-Perot cavity, equation (2) can be re-written, $$K(l, \lambda) = \frac{2}{1 + \frac{2R}{1-R}} \left[ \frac{1}{2} + \sum_{j=1}^{\infty} R^j \cos(2\pi j n\sigma l) \right]. \quad (4)$$

The form of equation (4) shows the presence in the signal of frequency components, $j\sigma$, that are harmonies of the fundamental spectral frequencies. The amplitude of these components decays with increasing harmonic number according to the cavity reflectance as given in equation (4). Since R is confined to be between zero and unity, only a finite number of harmonics will have amplitude above a given threshold. For a given signal threshold, ∈, the Nyquist-Shannon sampling limit is met with the condition, $$\delta \le \frac{\ln(R)}{4n\sigma_{max}\ln(\varepsilon)}, \quad (5)$$

where $\delta$ is the step size over the space l. A common convention in Fabry-Perot spectroscopy defines the reflecting finesse, $$F = \frac{\pi\sqrt{R}}{(1-R)}. \quad (6)$$

The reflecting finesse is the ratio of the fringe width to fringe period and is also approximately equal to the effective number of beams in a Fabry-Perot cavity. Applying the latter interpretation to equation (4) for a set of ideal Fabry-Perot cavities results in a Nyquist-Shannon criterion of $$\delta \le \frac{1}{4n\sigma_{max}F}. \quad (7)$$

2. Minimum wavenumber: The measurement in space must cover at least one full order of the minimum wavenumber present, $$\sigma_{min} \ge \frac{1}{2n(l_{max} - l_{min})} = \frac{1}{2nd_r}, \quad (8)$$

where $l_{min}$ and $l_{max}$ are the minimum and maximum cavity lengths used in the measurement, $d_r$ being their difference. In the case of N evenly sampled steps, equation (8) becomes $$\sigma_{min} \ge \frac{1}{2n(N-1)\delta}, \quad (9)$$

and happens to be equivalent to the frequency resolution in Fourier Transform spectroscopy. Note that in multiplexed Fabry-Perot spectroscopy, that the minimum frequency and frequency resolution are not equivalent.

3. Frequency resolution: The condition for resolvability of two frequencies over a range $d_r$ is that the number of periods for each frequency component differ by a factor greater than the width of one fringe. This can be stated as $$2nd_r(\sigma_2 - \sigma_1) \ge \frac{1}{F}, \quad (10)$$

where we have made use of the fact that the reflecting finesse is the ratio of fringe width to period. This leads to a minimum frequency resolution step of $$\Delta\sigma = \frac{1}{2nd_rF} = \frac{1}{2n(N-1)\delta F} \quad (11)$$

where the second equality only holds in the case of N evenly sampled steps.

In the general case, where the reflecting finesse and refractive index vary with the optical frequency, the guidelines above still should guide the design of measuring devices and recovery algorithms. The optical vacuum wavenumber, σ, and index, n can be replaced by a reduced optical wavenumber, $^{red}\sigma$, and reduced index, $\bar{n}$, where $^{red}\sigma = n(\sigma)\sigma/\bar{n}$ and $\bar{n}$ is any component of the refractive index invariant with frequency. The Nyquist-Shannon sampling criterion, given by inequality (7) must be then satisfied for every frequency to which the signal is sensitive. The minimum wavenumber of eqs. (8) and (9) depends trivially on the frequency through the refractive index, and is still an easily calculated scalar quantity (except in the case of anomalous dispersion at this wavenumber.) The resolution of equation (11) becomes frequency dependent through both the index and finesse, and can be calculated separately for each wavenumber of interest.

For the case where the reflectance is constant over the wavenumber range of interest, and N evenly spaced steps define the Fabry-Perot cavity sampling, two descriptive special results follow from the first three conditions above.

Special Result 1, Resolving power: Using equation (11) and the equality condition in inequality (7), the maximum resolving power can be shown to be $$\frac{\sigma_{max}}{\Delta\sigma} = \frac{N-1}{2}. \quad (12)$$

Note that within the limits of the Nyquist-Shannon sampling [eq. (7)] and a scan that extends at least over one complete order of the minimum frequency, the resolving power of the instrument depends only on the number of measurements.

Special Result 2, Number of resolved spectral elements: An expression for the maximum number of resolved spectral elements for a multiplexed Fabry-Perot instrument can be derived using equation (12) and the ratio of minimum wavenumber [given in the equality of inequality (9)] and the resolution [given in equation (11)]. This yields, $$\# RSEs = \frac{\sigma_{max} - \sigma_{min}}{\Delta\sigma} = \frac{N-1}{2} - F. \quad (13)$$

Therefore, the number of resolved spectral elements is maximized with a large number of measurements and a finesse that is small relative to the number of measurements. For very high finesse, multiplexed measurement of spectra becomes not optimal, but then optical bandwidth must be reduced. Equations (12) and (13) are not generally valid for broadband instruments where the reflectance varies as a function of optical frequency. The special results of equations (12) and (13) are useful for comparing this type of spectroscopy with other multiplexed spectroscopy techniques, chiefly, Fourier Transform Spectroscopy.

The above three conditions and their description in equations (5)-(13) are meant to guide device design and are optionally useful in practicing one or more embodiments of the instant invention. These conditions, define the appropriate wavenumbers over which a spectrum can be reconstructed given an axis l, over which a measurement is made. Likewise, the above conditions can be used to find the measurement axis required for numerically stable recovery of a spectrum on a given axis. While equations (9) and (11)

address cases where the l axis is sampled evenly, this is not a requirement of this invention. An embodiment of the instant invention is applied to uneven spacing in the l axis, provided that the Nyquist-Shannon sampling criterion [eq. (7)] and minimum wavenumber requirement [eq. (8)] are met. These conditions generally give the conditions for a numerically stable solution of equation (1) for all multiplexed Fabry-Perot spectroscopy techniques.

Other Instrumental Embodiments

For the embodiment of a scanning Fabry-Perot interferometer, equation (11) shows that the frequency resolution is modified from that expected from an unmultiplexed Fabry-Perot measurement by a factor of $1/d_r$. This means that the resolution from a non-multiplexed Fabry-Perot scan can be equaled by a multiplexed Fabry-Perot scan that starts at the same point and proceeds to a value of l that is twice as large as the starting value. Alternatively, if one scans a Fabry-Perot interferometer inward from some distance $l_0$ to $l_0/2$, the resolution penalty for multiplexing is a factor of 2 relative to a local scan around $l_0$ and there is no resolution penalty relative to a local scan around $l_0/2$.

In an embodiment of an array of etalons, whether affixed to an array of detectors, or coupled to a detector or detectors by some imaging optics or some other means, the etalons may be ordered, or disordered. This embodiment of the invention uses an evenly spaced, ordered array of etalons, such as shown in FIG. 1. This embodiment measures the signal of multiple order etalons. The preferred embodiment also has the etalons in close contact with an image sensor. In this configuration, the device can be used as a line scanning, imaging spectrometer, or a standalone spectrometer. When used as an imaging spectrometer, a component of a scene can be scanned across each etalon. Alternatively, lines of an image can be scanned across the etalon staircase.

Embodiments of the instant invention are optionally used for electromagnetic waves that are non-optical. For example, microwave, or radiowave spectral analysis based on reflective cavities would be possible using an embodiment of the instant invention.

This written description sets forth the best mode of the invention and provides examples to describe the invention and to enable a person of ordinary skill in the art to make and use the invention. This written description does not limit the invention to the precise terms set forth. Thus, while the invention has been described in detail with reference to the examples set forth above, those of ordinary skill in the art may effect alterations, modifications and variations to the examples without departing from the scope of the invention.

These and other implementations are within the scope of the following claims.

What is claimed as new and desired to be protected by Letters Patent of the United States is:

1. A method comprising:
   receiving a signal from a Fabry-Perot interferometer;
   sampling the signal according to a generalized Nyquist-Shannon sampling criterion;
   sampling the signal according to a phase differential criterion for wave number resolution; and
   reconstructing an input spectrum for the signal based on the signal sampled according to the generalized Nyquist-Shannon sampling criterion and the signal sampled according to the phase differential criterion for wave number resolution,
   wherein the Fabry-Perot interferometer comprises a substrate; and a plurality of etalon cavities one of affixed to and coupled to the substrate, the plurality of etalon cavities comprising a plurality of cavity thicknesses;
   wherein each etalon cavity of said plurality of etalon cavities comprises a respective height value, said each etalon cavity of said plurality of etalon cavities having an associated next highest height value etalon cavity of said plurality of etalon cavities, said associated next hi est height value etalon cavity of said plurality of etalon cavities comprising a next highest height value, said each etalon cavity of said plurality of etalon cavities having an associated next lowest height value etalon cavity of said plurality of etalon cavities, said associated next lowest height value etalon cavity of said plurality of etalon cavities comprising a next lowest height value, a difference between the next highest height value and the respective height value satisfying the generalized Nyquist-Shannon sampling criterion a difference between the respective height value and the next lowest height value satisfying the generalized Nyquist-Shannon sampling criterion, and
   wherein said plurality of cavity thicknesses comprises a maximum height value and a minimum height value, a difference between said maximum height value and minimum height, value is at least an overall height range, said overall height range satisfying the phase differential criterion for wavenumber resolution.

2. The method according to claim 1, further comprising:
   providing one of a detector and an image sensor,
   wherein the generalized Nyquist-Shannon sampling criterion comprises:

$$d \leq \frac{1}{4Fns_{max}},$$

where d is a step size, F is a cavity finesse, n is a cavity refractive index, and $s_{max}$ is a maximum vacuum wavenumber to which the one of a detector and an image sensor coupled to the Fabry-Perot interferometer is sensitive.

3. The method according to claim 1, wherein the phase differential criterion for wavenumber resolution comprises:

$$d_r \leq \frac{1}{2Fn\Delta s},$$

where $d_r$ is said overall height range, F is a cavity finesse, n is a refractive index of a cavity, and $\Delta s$ is a vacuum wavenumber resolution.

4. The method according to claim 2, wherein said image sensor comprises a two-dimensional focal plane array;
   wherein said detector comprises one of a point detector, a linear array detector, and a two-dimensional array detector.

* * * * *